United States Patent [19]

Koster et al.

[11] Patent Number: 5,445,949
[45] Date of Patent: Aug. 29, 1995

[54] LARGE SCALE SEPARATION AND PURIFICATION OF FERMENTATION PRODUCT

[75] Inventors: Frans Koster, Delft; Jos J. P. Webbers, Maassluis, both of Netherlands

[73] Assignee: Gist-Brocades N.V., Netherlands

[21] Appl. No.: 326,315

[22] Filed: Oct. 20, 1994

Related U.S. Application Data

[63] Continuation-in-part of Ser. No. 64,719, May 18, 1993.

[30] Foreign Application Priority Data

May 19, 1992 [EP] European Pat. Off. ............ 92201435

[51] Int. Cl.$^6$ ................ C12N 9/30; C12N 9/00; C12P 21/06
[52] U.S. Cl. ................ 435/71.1; 435/71.2; 435/71.3; 435/183; 435/187; 435/198; 435/272; 435/800; 435/814; 435/815; 435/816; 435/874
[58] Field of Search ............ 435/71.1, 71.2, 71.3, 435/183, 187, 198, 272, 800, 814, 815, 816, 874

[56] References Cited

U.S. PATENT DOCUMENTS

| | | | |
|---|---|---|---|
| 2,669,559 | 2/1954 | Reid | 435/815 |
| 2,952,586 | 9/1960 | Okunuki et al. | 435/815 |
| 3,098,015 | 7/1963 | Ayrapa et al. | 435/816 |
| 3,184,394 | 5/1965 | Schmidtberger et al. | 435/815 |
| 3,208,918 | 9/1965 | Beers | 435/815 |
| 3,252,961 | 5/1966 | Ropeers et al. | 426/656 |
| 3,262,863 | 7/1966 | Fukomoto et al. | 435/816 |
| 3,269,918 | 8/1966 | Barton et al. | 435/815 |
| 3,695,999 | 10/1972 | Forgione et al. | 435/816 |
| 3,728,224 | 4/1973 | Burglum | 435/814 |
| 3,775,254 | 11/1973 | Buetow | 435/815 |
| 3,810,823 | 5/1974 | Fujii et al. | 435/815 |
| 4,016,039 | 4/1977 | Schreiber | 435/816 |
| 5,124,256 | 6/1992 | Crahay et al. | 435/71.1 |
| 5,208,156 | 5/1993 | Shibatani et al. | 435/196 |
| 5,227,300 | 7/1993 | Holmes et al. | 435/198 |
| 9,203,127 | 11/1992 | Holmes . | |

FOREIGN PATENT DOCUMENTS

| | | |
|---|---|---|
| 0130064 | 1/1985 | European Pat. Off. . |
| 0167309 | 1/1986 | European Pat. Off. . |
| 0334462 | 9/1989 | European Pat. Off. . |
| PCT/NL860-0023 | 2/1987 | WIPO . |
| PCT/US900-0756 | 9/1990 | WIPO . |

OTHER PUBLICATIONS

Copy of Mitsubishi Gas Chem. KK (1 page) No. JP2109974.
Copy of Derwent Pub. Ltd. AN 90–168352 (22) (1 page).
Copy of Search Report—European—(1 page).
Cpy of Database WPI Section CH, Week 9007.
Copy of Derwent Publications Ltr. (1 page).

*Primary Examiner*—Herbert J. Lilling
*Attorney, Agent, or Firm*—Bierman and Muserlian

[57] ABSTRACT

A method of separating a hydrophobic fermentation product selected from the group consisting of lipase, esterase, endoxylanase and an antibiotic from a mixture comprising said product and contaminants which method comprises adding to the mixture sequentially (1) 0.5 to 15% (w/v) of a nonionic surfactant, (2) 0.5 to 60 mg of a flocculating agent per gram of said mixture, (3) 1 to 20% (w/v) of an extra nonionic surfactant, (4) a suitable K, Na, NH$_4$ or Mg salt selected from the group of chlorides, sulfates, acetates, carbonates or phosphates, whereby the concentration of the salt is chosen so as to have the surfactant layer on top and is between 2 and 30%;

to obtain a three phase product mixture, separating the product mixture into liquid-liquid-solid fractions and recovering the hydrophobic fermentation product.

19 Claims, 1 Drawing Sheet

LARGE SCALE SEPARATION AND PURIFICATION OF FERMENTATION PRODUCT

PRIOR APPLICATION

This application is a continuation-in-part of U.S. patent application Ser. No. 064,719 filed May 18, 1993.

The present invention relates to a method to separate soluble or membrane associated bound fermentation products with a hydrophobic character from cell solids, hydrophilic proteins and other contaminants.

STATE OF THE ART

Liquid phase separation with amphiphilic detergents is a technique that uses the protein-solubizing ability of the detergent. A method of separating integrate membrane proteins from soluble proteins is described by Brodier (1981). The phases are separated by increasing the temperature of the mixture above the cloud point of the detergent. The detergent phase is the lower phase and is in the form of oily droplets.

Another way to cause phase separation is described by Parish (1986). According to this method, a lysate is separated in the presence of ammonium sulfate. In most cases, the detergent phase is the lower phase. Only at very high ammonium sulfate concentrations ($>12\%$) is the detergent phase the upper layer. The enormous amounts of ammonium sulfate used are economically very unattractive. In all cases, the cells are separated before the extraction procedure is carried out.

In conventional industrial processes, several steps are involved in recovering the desired fermentation product. It is usually necessary to carry out at least separation, concentration and purification steps. When hydrophobic proteins are involved, separation from cells becomes more difficult and further steps may be necessary. Neither of the above described processes is therefore satisfactory for the separation of a fermentation broth into fractions.

OBJECTS OF THE INVENTION

It is an object of the invention to provide a process for the separation, concentration and purification of fermentation products such as hydrophobic proteins from a fermentation broth in one step, particularly so that microorganisms may be separated from the desired hydrophobic product.

These and other objects and advantages of the invention will be come obvious from the following detailed description.

THE INVENTION

The present invention therefore provides a process for the separation of hydrophobic fermentation products such as antibiotics and proteins from a mixture comprising said product and contaminants which method comprises adding to the mixture simultaneously or sequentially, (1) 0.5 to 15% of a nonionic surfactant;

(2) 0.5 to 60 mg of a flocculating agent per gram of said mixture;

(3) 1 to 20% (w/v) of an extra surfactant; and (4) a suitable K, Na, $NH_4$ or Mg salt selected from the group of chlorides, sulfates, acetates, carbonates or phosphates, whereby the concentration of the salt is chosen so as to have the surfactant layer on top and is between 2 and 30%;

to obtain a product mixture, separating the product mixture into fractions and recovering the hydrophobic product.

The process of the present invention is preferably an aqueous two-phase separation and is preferably carried out in a single step.

The broth from which the desired product is separated is generally a fermentation broth, usually containing cell solids, hydrophilic proteins and other contaminants.

A suitable microorganism is generally used to produce the broth. Suitable microorganisms include fungi, yeast and bacteria. The process of the present invention is particularly suitable for the separation and purification or hydrophobic fermentation products of microorganisms having lengths of from 0.2 to 1.5 μm, such as *E. coli, Serratia marcescens* or Pseudomonas.

Hydrophobic compounds are defined as compounds that are slightly soluble in water in the absence of detergent; but the hydrophobicity of compounds meant here can be strongly influenced by salts. Examples of hydrophobic proteins are hydrophobic membrane proteins such as Cytochrome C oxidase, low density lipoproteins, ATP-ase, esterase, lipase and endoxylanase, and extracellular hydrophilic proteins such as protease and amylase. The proteins may be soluble or membrane associated bound proteins. An example of a hydrophobic antibiotic is natamycin. Hydrophobicity may be altered by changing the concentration of salts such as chlorides, sulfates and phosphates.

The optional addition of divalent cations in step (1) stabilizes and pre-flocculates the broth. Suitable divalent cations include $MgCl_2$ and $CaCl_2$. The suitability of the cation depends on the microorganism used and the protein which the microorganism is producing. $CaCl_2$ is preferably used.

The addition of the nonionic surfactant in step (1) drives the hydrophobic product from the cell walls and prevents adsorption of the hydrophobic product to surfaces. Suitable surfactants contain both a hydrophilic, water soluble group and a hydrophobic, water-insoluble group. Such surfactants are termed "amphiphiles" and are characterized by their critical micelle concentration (CMC), preferably between 100–500 μM, the concentration at which unassociated surfactant molecules aggregate into micelles and by their hydrophilic-lipophilic balance (HLB), preferably between 10–18, a number indicating the proportion of hydrophilic to hydrophobic portions of the molecule.

Suitable surfactants are, for example oxyethylated alkylphenol such as Triton types; ethylene oxide-propylene oxide condensates (Pluronic block copolymers) such as described in U.S. Pat. No. 2,674,619; polyoxyethylene fatty alcohol ethers (Brij); polyoxyethylated derivatives of partial esters of C12–C22 fatty acids made by adding polyoxyethylene chains to the nonesterified hydroxyls (Tweens).

Preferred amphiphilous for use in this invention are nonionic surfactants. The most preferred amphiphiles are the nonionic surfactants having a high water solubility and selected from the group consisting of substances having the general formula $RC_6H_4(OC_2H_4)_nOH$ wherein R is octyl or nonyl and n is at least 3, preferably n is between 5 and 15. A most preferred substance of the foregoing general formula is octyl phenoxy polyethoxy ethanol. Surfactants of this type are available commercially under the trademark "Triton X", e.g. Triton X-45, Triton X-100, Triton X-102 and Triton X-114.

Addition of a flocculating agent increases the sedimentation of the cells. Suitable flocculating agents are for example: quaternised polyamines, acrylamide acrylate copolymers or cationic polysaccharides from deacylated chitin.

Extra surfactant is added in step (3) to form a liquid surfactant phase which is formed on top of the aqueous phase. The aqueous phase contains the hydrophilic product, unwanted contaminants and cell-solids. The sursurfactants used in step (3) are selected from the those which may be used in step (1). A suitable salt is then added.

Suitable salts are for example: chlorides, such as KCl or NaCl, sulfates such as $MgSO_4$ or $Na_2SO_4$ or phosphates. The concentration of the salt is chosen so as to have the surfactant layer on top and is between 2 and 30%, preferably between 4 and 15% (v/v).

The resulting liquid comprises an upper layer of liquid surfactant which contains the hydrophobic product, a lower, aqueous layer containing unwanted proteins and contaminants and, at the bottom, flocculated cells. Separation of the fractions therefore results in separation of the hydrophobic compounds from the other compounds and cell debris.

The fraction may be separated by any conventional technique, such as centrifugation or sedimentation. The liquid surfactant may be further concentrated by removing water, surfactant and salts, for example, by using a precipitation process, followed by a drying step.

The process of the present invention can be advantageously used to purify antibiotics having a hydrophobic character such as natamycin. Natamycin can be produced by species of e.g. Streptomyces. An example of a suitable species is *Steptomyces natalensis*.

The process of the present invention is particularly suitable for separation and purification of enzymes, preferably lipolytic enzymes, more preferably fungal and bacterial lipases, esterases, phospholipases and lipoprotein lipases. r-DNA techniques make mutations of enzymes possible. Such modified enzymes show improved qualities in an industrial use. These modified enzymes are also comprised in the scope of the present invention. The lipases according to the present invention are preferably those which may be used in the hydrolysis of tri-acyl glycerides. The enzyme catalyzes hydrolysis of tri-acyl glycerides to produce fatty acids, monoglycerides, diglycerides and glycerol.

Lipases which may be purified according to the present invention are generally produced by microorganisms such as: species from Pseudomonas, Aspergillus, and Mycobacterium, Mycotorula lipolytica, Sclerotina, Fusarium oxysporum and Actinobacter calcoaceticus. Examples of suitable Pseudomonas species are *Pseudomonas fluorescens, Pseudomonas stutzeri, Pseudomonas aeruginosa, Pseudomonas putida, Pseudomonas fragi, Pseudomonas alcaligenes, Pseudomonas pseudoalcaligenes* and *Pseudomonas glumae*.

Pseudomonas strains which can be advantageously used to produce lipases are for example:
*Pseudomonas pseudoalcaligenes* CBS 467.85
*Pseudomonas pseudoalcaligenes* CBS 468.85
*Pseudomonas pseudoalcaligenes* CBS 471.85
*Pseudomonas pseudoalcaligenes* CBS 473.85
*Pseudomonas pseudoalcaligenes* ATCC 17440
*Pseudomonas alcaligenes* ATCC 31371
*Pseudomonas alcaligenes* ATCC 31372
*Pseudomonas alcaligenes* ATCC 53877
*Pseudomonas alcaligenes* ATCC 14909
*Pseudomonas aeruginosa* ATCC 19154
*Pseudomonas aeruginosa* ATCC 136.89

It will be appreciated that other suitable microorganisms may be used as well.

According to a preferred embodiment of the present invention, the process for producing lipase comprises the following steps:

(1) aerobically cultivating a suitable strain of microorganism, preferably of the species *Pseudomonas pseudoalcaligenes, Pseudomonas alcaligenes* or *Pseudomonas aeruginosa* under conditions suitable for the formation of the lipase in the cells whereby the cells are present in a suitable nutrient culture medium containing assimilable sources of carbon, nitrogen and inorganic minerals; and (2) separating the lipase so produced from the fermentation broth according to methods described hereinabove.

The fermentation of the lipase producing cells will usually be at a temperature of about 5° to 45° C. at a pH of 5 to 12. Culture media include nutrient growth media (commercially available) or a defined medium containing complex N and C-sources and inorganic materials.

The lipase produced according to the process of the present invention is more than 90% (by weight) pure on basis or protein. Conventional single step separations carried out on industrial scale usually give protein of interest with a purity of maximal 50%, depending on the fermentation broth.

It is particularly surprising that a purity of 90% is obtained for lipases produced from Pseudomonas strain; Pseudomonas microorganisms are so small that separation problems usually occur. For example, the *Pseudomonas alcaligenes* or *Pseudomonas pseudoalcaligenes* are microorganisms which have a size of less than 1 μm.

Lipase originating from *Pseudomonas alcaligenes* or pseudoalcaligenes having a purity of more than 90 wt % and advantageously 98 wt % of the protein fraction may be produced according to the process of the present invention.]

Lipase originating from *Pseudomonas pseudoalcaligenes* (CBS 473.85) and produced on industrial scale by the process of the present invention showed the following characteristics:
purity of 90% or more on basis of protein; and
a molecular weight of 31 kD.

The hydrophobic protein separated and purified according to the present invention can be further formulated in various forms.

For example, proteins such as lipase can be formed into a powder or can be encapsulated in an agent such as polyethylene glycol. The lipase produced according to the process of the present invention may be used in powder detergents and liquid detergents. A typical lipase powder has the following characteristics:
10 to 30% w/w lipase;
12 to 33% w/w protein, including the lipase; and
88 to 67% w/w non-protein compounds for example water, surfactants and salts added during the separation and purification of lipase.

When the protein purified by the process of the invention is formulated into a detergent, a surfactant is generally included to improve water contact with the protein.

The lipase produced according to the present invention is advantageously encapsulated. Granules or prills can be prepared containing 5 to 15% lipase and 95 to 85% filling materials such as polyethylene glycol (PEG). The encapsulating materials when contacted with water will disintegrate and the lipase is available for bioconversion. Granules or prills can be prepared according to methods which are generally known in this specific area of the art.

In a specific embodiment of the invention, the enzymatic detergent additive is provided in liquid form with an enzyme stabilizer. This stabilizer is e.g. propylene glycol. Such liquid additives are preferably used in liquid detergent compositions.

When lipase producing microorganisms known in the prior art are applied in the present process, a lipase product is obtained which has an unexpectedly high purity compared to the lipases produced and separated according to known processes.

All publications and patent applications cited in this specification are herein incorporated by reference as if each individual publication or patent application were specifically and individually indicated to be incorporated by reference.

Figure 1:
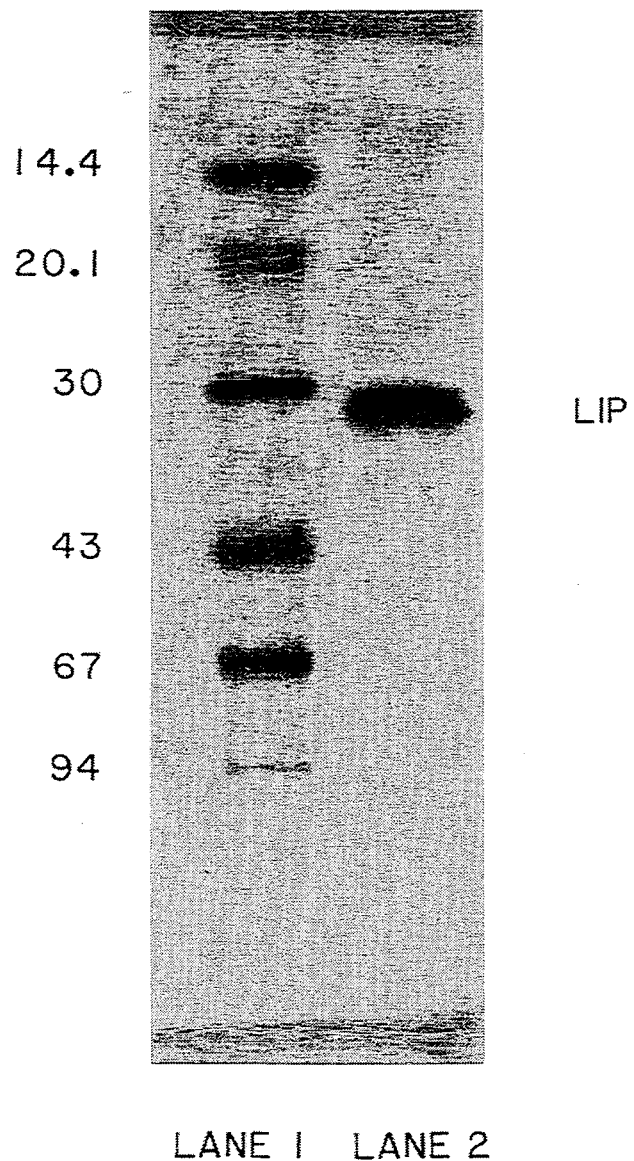
FIG. 1 illustrates the purity of the product determined by SDS-page.

Legend to the Figure.

Determination of the purity of lipase produced using SDA page.

FIG. 1, lane 1: marker proteins with known mol. wt in kD;

FIG. 1, lane 2: lipase produced according to the invention.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit and scope of the appended claims.

The following experimental data are given to illustrate the invention. It has to be understood that a person skilled in the art who is familiar with the methods may use other lipase producing strains which can be equally used for the purpose of the present invention. These alterations are included in the scope of the invention.

EXAMPLE 1

To 165 l of a broth of *Pseudomonas pseudoalcaligenes* (CBS 473.85), containing lipase, 9.24 l of a 20% Triton X-114 solution in water was added, followed by 73.9 l of a 1% solution of Chitosan in 0.4% acetic acid in water. The mash was mixed well after each addition. After the additions, the pH was 5.9. After addition of another 43.5 l of 20% Triton X-114, 35 kg of dry NaCl were added under constant stirring.

The mixture was separated in a continuous 3 phase separator of the centrifugal disk type at 8000 g and at 10° C., resulting in 25 l of light (product) phase containing lipase, 31 l of concentrated cells and 250 l of salt solution and rinsewater.

EXAMPLE 2

To 1550 l of *Pseudomonas pseudoalcaligenes* (CBS 473.85) mash containing lipase, first 34 l of a 25% $CaCl_2$ solution in water was added, followed by 95 l of a 20% solution of Triton X-114 in water. The mash was stirred during the additions.

Mixing was stopped and 700 l of a 1% solution of chitosan in 0.4% acetic acid in water was added on top.

After high speed mixing for 5 minutes to achieve a good flocculation, the mixing speed was reduced and 450 l of a 20% solution of Triton X-114 in water was added, followed by 635 l of a solution of 75% $MgSO_4.7H_2O$ in water. The pH was 5.9.

A part of the mixture (191 l) was separated in a continuous separator of the above mentioned type at 8000 g and a temperature of 10° C., resulting in 20 l of the light (product) phase containing 80 wt % lipase, 26 l of concentrated cells and 776 l of the salt solution.

The purity of the product was determined with SDS-page, showing one single band at 31 kD, see FIG. 1.

EXAMPLE 3

To 100 ml of broth (containing $CaCl_2$) of *Pseudomonas pseudoalcaligenes* (CBS 473.85) containing lipase, 6 ml of a 20% Triton X-114 solution in water were added, followed by 45 ml of a flocculant solution (specified below). The mash was mixed well after each addition. After the additions, the pH was between 5.7 and 6.3.

After addition of another 29 ml of 20% Triton X-114, 26.5 g of solid $MgSO_4.7H_2O$ were added under constant stirring.

The mixture was separated in three phases in a small scale centrifuge of the swing out type at 2000 g and at 20° C., resulting in a top phase of 8–12% containing lipase and a salt-cell phase containing the impurities.

Flocculants used: Alcofix 109, Magnofloc 368, Superfloc C-498, WT-20 or A-50.

EXAMPLE 4

To 100 ml of broth (containing $CaCl_2$) of *Pseudomonas pseudoalcaligenes* (CBS 473.85) containing lipase, 6 ml of a 20% Triton X-114 solution in water were added, followed by 45 ml of a 0.5% chitosan solution in 0.2% acetic acid in water. The mash was mixed well after each addition. After the additions, the pH was between 5.7 and 6.3.

After addition of another 29 ml of 20% Triton X-114, a salt solution (specified below) to end concentration between 6–29% was added under constant stirring.

The mixture was separated in three phrases in a small scale centrifuge of the swing out type at 2000 g and at 20° C., resulting in a top phase of 7–15% containing lipase and a salt-cell phase containing the impurities.

Salts used: $Na_2SO_4$, $KH_2PO_4$, $KHCO_3$, $KCl$, $CaCl_2$, $Na_3PO_3.8H_2O$, $C_2Na_2O_2$ or $C_6H_5Na_3O_7.2H_2O$.

EXAMPLE 5

To 100 ml of whole broth of *Pseudomonas pseudoalcaligenes* (CBS 473.85) containing lipase, 0.58 ml of a 33% $CaCl_2$ was added, followed by 6 ml of a 20% Triton X-114-, Nonident NP-40-, Marlophen 87-, or Marlophen 88 solution, followed by 35 ml of a 0.64% chitosan solution in 0.26% acetic acid in water. The mash was mixed well after each addition. After the additions, the pH was between 5.6 and 6.3.

Under constant stirring, another 29 ml of 20% solutions of the above mentioned detergents and 35 ml of 57% $MgSO_4.7H_2O$ in water were added. A part of the mixture was separated in a centrifuge at 2500 g and ambient temperature, resulting in 9–12 vol % of light (product) phase containing lipase, 12–14.5 vol % of concentrated cells and 70–89 vol % of salt solution depending on the detergent used.

EXAMPLE 6

To 100 ml of broth of *Pseudomonas aeruginosa* (CBS 136.89) containing lipase, 0.58 ml of a 33% CaCl$_2$ was added, followed by 6 ml of a 20% Triton X-114-, Nonident NP-40-, Marlophen 87-, or Marlophen 88 solution, followed by 35 ml of a 0.64% chitosan solution in 0.26% acetic acid in water. The mash was mixed well after each addition. After the additions, the pH was between 5.6 and 6.3.

Under constant stirring, another 29 ml of 20% solutions of the above mentioned detergents and 35 ml of 57% MgSO$_4$.7H$_2$O (w/w) in water were added.

A part of the mixture was separated in a centrifuge at 2500 g and ambient temperature, resulting in 10–20 vol % of light (product) phase containing lipase, 1–2.5 vol % of solids and 80–88 vol % of salt solution depending on the detergent and salt concentration used.

EXAMPLE 7

To 100 ml of whole broth of *Bacillus stearothermophilus* (NCIMB 40221) containing endoxylanase, 0.76 g of a 33% CaCl$_2$ solution was added, followed by 6 ml of a 20% Triton X-114 solution and followed by addition of 45 ml of a 0.5% chitosan solution in 0.2% acetic acid in water. The mash was mixed well after each addition.

Under constant stirring, another 29 ml of 20% Triton X-114 and 26.5 g of solid MgSO$_4$.7H$_2$O were added.

A part of the mixture was separated in a centrifuge at 2500 g and ambient temperature, resulting in 11 vol % of light (product) phase containing endoxylanase, 4–5% of concentrated cells and 84–85 vol % of salt solution.

EXAMPLE 8

To 100 ml of broth of *Streptomyces natalensis* (CBS 700.57) containing natamycin, 0.58 ml of a 33% CaCl$_2$ was added, followed by 6 ml of 20% Triton X-114, Nonidet NP-40-, Marlophen 87-, or Marlophen 88 solution, followed by 35 ml of a 0.64% chitosan solution in 0.26% acetic acid in water. The mash was mixed well after each addition. After the additions, the pH was between 5.6 and 6.3.

Under constant stirring, another 29 ml of 20% solutions of the above mentioned detergents and 35 ml of 57% MgSO$_4$.7H$_2$O (w/w) in water was added.

A part of the mixture was separated in a centrifuge at 2500 g and ambient temperature, resulting in 10–15 vol % of light (product) phase containing natamycine, 5–10 vol % of solids and 75–85 vol % of salt solution depending on the detergent and salt concentration used.

What we claim is:

1. A method of separating a hydrophobic fermentation product selected from the group consisting of lipase, esterase, endoxylanase and an antibiotic from a mixture comprising said product and contaminants which method comprises adding to the mixture sequentially (1) 0.5 to 15% (w/v) of a nonionic surfactant,
   (2) 0.5 to 60 mg of a flocculating agent per gram of said mixture,
   (3) 1 to 20% (w/v) of an extra nonionic surfactant,
   (4) a suitable K, Na, NH$_4$ or Mg salt selected from the group consisting of chlorides, sulfates, acetates, carbonates or phosphates, whereby the concentration of the salt is chosen so as to have the surfactant layer on top and is between 2 and 30%;

to obtain a three phase product mixture, separating the product mixture into liquid-liquid-solid fractions and recovering the hydrophobic fermentation product.

2. A method according to claim 1 which further comprises adding a divalent cation prior to adding the nonionic surfactant.

3. A method according to claim 1 wherein the fermentation product is a protein or is an antibiotic.

4. A method according to claim 3 wherein the protein is a lipase.

5. A method according to claim 4 wherein the lipase has a molecular weight of 31 kD.

6. A method according to claim 1 wherein the mixture is a microbial fermentation broth.

7. A method according to claim 6 wherein the microorganism is *Pseudomonas pseudoalcaligenes, Pseudomonas alcaligenes* or *Pseudomonas aeruginosa.*

8. A method according to claim 1 which further comprises a concentration step.

9. A method according to claim 1 which further comprises purifying the hydrophobic fermentation product to a purity of 90 wt % or more on basis of fermentation product.

10. A method according to claim 9 wherein the fermentation product is purified to a purity of 93 wt % or more on basis of fermentation product.

11. A method according to claim 1 which further comprises formulating the purified fermentation product into a powder.

12. A method according to claim 11 wherein the fermentation product powder comprises an effective amount to improve water contact with a protein in the range up to 40 by wt % of a nonionic surfactant.

13. A method according to claim 3 which further comprises formulating the purified protein into a composition containing 5 to 20% w/w of protein and 80 to 95% w/w encapsulating agent, filling agent and/or stabilizing agent.

14. A method according to claim 3 which further comprises formulating the purified protein into a detergent composition comprising 0.01–50% protein.

15. A method according to claim 3 wherein the protein is a lipase and which process further comprises hydrolysing tri-acyl glycerides with the lipase.

16. A method according to claim 6 wherein the microorganism is selected from Pseudomonas, Aspergillus, Mycobacterium, *Mycotorula lipolytica,* Sclerotina, *Fusarium oxysporum* and *Actinobacter calcoaceticus.*

17. A method of claim 3 wherein the protein is an enzyme.

18. A method of claim 18 wherein the enzyme is selected from the group consisting of esterase, lipase, or endoxylanase.

19. A method of claim 3 wherein the antibiotic is natamycin.

* * * * *